United States Patent
Schloss

(10) Patent No.: US 7,250,401 B2
(45) Date of Patent: Jul. 31, 2007

(54) THERAPEUTIC COMPOSITIONS

(75) Inventor: John V. Schloss, Valencia, CA (US)

(73) Assignee: Advanced Therapeutics and Diagnostics, LC, Lawrence, KS (US)

(*) Notice: Subject to any disclaimer, the term of this patent is extended or adjusted under 35 U.S.C. 154(b) by 123 days.

(21) Appl. No.: 10/841,950

(22) Filed: May 7, 2004

(65) Prior Publication Data

US 2005/0130904 A1 Jun. 16, 2005

Related U.S. Application Data

(63) Continuation of application No. PCT/US02/35930, filed on Nov. 8, 2002.

(60) Provisional application No. 60/356,903, filed on Feb. 12, 2002, provisional application No. 60/348,861, filed on Nov. 9, 2001.

(51) Int. Cl.
*A61K 38/00* (2006.01)

(52) U.S. Cl. .......................................... 514/19; 530/332

(58) Field of Classification Search .................... None
See application file for complete search history.

(56) References Cited

U.S. PATENT DOCUMENTS 6,156,794 A * 12/2000 Faiman et al. ............... 514/478

FOREIGN PATENT DOCUMENTS

WO    WO-98/19676    5/1998

* cited by examiner

*Primary Examiner*—Paul A. Zucker
(74) *Attorney, Agent, or Firm*—Schwegman, Lundberg, Woessner & Kluth

(57) ABSTRACT

A method is provided for the preparation of compounds of the formula $(R^1)(R^2)NC(=X)S(O)_nR^3$ or $(R^1)(R^2)NC(=X)OS(O)_nR^3$, wherein $R^1$, $R^2$ and $R^3$, X and n have any of the meanings defined in the specification. A method is also provided for the detection and quantitation of compounds of the formula $(R^1)(R^2)NC(=X)OS(O)_nR^3$. A method to link a therapeutic agent to a compound that is conjugated to glutathione is also provided for the purpose of improving the therapeutic properties of the therapeutic agent. Novel compounds, intermediates, pharmaceutical compositions and methods of use are also provided.

17 Claims, 4 Drawing Sheets carbamoyl thioester sulfoxide
for $R^1 = R^2 = C_2H_5$; $R^3 = CH_3$
the structure is DETC-MeSO carbamoyl sulfenate
for $R^1 = R^2 = C_2H_5$; $R^3 = CH_3$
the structure is DECOSMe carbamoyl thioester sulfone
for $R^1 = R^2 = C_2H_5$; $R^3 = CH_3$
the structure is $DETC\text{-}MeSO_2$ carbamoyl sulfinate
for $R^1 = R^2 = C_2H_5$; $R^3 = CH_3$
the structure is $DECO_2SMe$ carbamoyl sulfinate
for $R^1 = R^2 = C_2H_5$; $R^3 = CH_3$
the structure is $DECO_2SMe$ Oxidation carbamoyl sulfonate
for $R^1 = R^2 = C_2H_5$; $R^3 = CH_3$
the structure is $DECO_3SMe$ carbamoyl thioester sulfone
for $R^1 = R^2 = C_2H_5$; $R^3 = CH_3$
the structure is DETC-MeSO$_2$ glutathione S-carbamoyl glutathione
for $R^1 = R^2 = C_2H_5$
the structure is carbamathione and $R^3\text{-SO}_2^-$ for $R^3 = CH_3$
the structure is methyl sulfinate

US 7,250,401 B2

THERAPEUTIC COMPOSITIONS

PRIORITY OF INVENTION

This application is a continuation under 35 U.S.C. 111(a) of PCT/US02/35930, filed Nov. 8, 2002 and published in English on Jul. 3, 2003 as WO 03/053337 A2, which application claims priority from U.S. Provisional Application Nos. 60/348,861 filed Nov. 9, 2001, and 60/356,903 filed Feb. 12, 2002.

GOVERNMENT FUNDING

The invention described herein was made with United States Government support under Grant Number N00014-94-1-0457 and N00014-00-1-0102 awarded by the Office of Navel Research. The United States Government has certain rights in this invention.

FIELD OF THE INVENTION

The present invention provides compounds and methods for their synthesis and use. The compounds of the invention are useful for treating glutamate-related diseases and for deterring ethanol consumption. The compounds of the invention are also useful as intermediates for preparing compounds that are conjugated with glutathione and linked to a therapeutic agent.

BACKGROUND OF THE INVENTION

The directed delivery of therapeutic agents to their site of action in the human body (e.g., antibiotics, drugs for the treatment of cancer, neuroprotective drugs or drugs for the treatment of any disorder), offers great advantages over a systemic administration of therapeutic agents.

Particularly useful would be compounds and methods to deliver therapeutic agents across the blood-brain barrier to the central nervous system or to the inner ear. This type of delivery would allow therapeutic agents to be specifically targeted to produce a neuroprotective therapeutic effect. Delivery of compounds across the blood-brain barrier can be mediated by glutathione-conjugation as described in U.S. Pat. No. 6,156,794.

Thus, there is a need for synthetic methods to prepare a compound that can be linked to a therapeutic agent and conjugated with glutathione to provide directed delivery.

Certain specific carbamoyl thioesters have also been used to deter ethanol consumption and to treat glutamate-related disorders, as described in U.S. Pat. Nos. 5,153,219 and 6,156,794.

There exists a need for additional methods and compositions to deter ethanol consumption by humans and to treat glutamate-related disorders (such as glutamate-related neurodegenerative disorders) with non-toxic glutamate antagonists.

SUMMARY OF THE INVENTION

The invention is based on the discovery of new compounds, compositions and methods that can be used to link a therapeutic agent to a compound that can be conjugated to glutathione. Such conjugated compounds facilitate the directed delivery of the linked therapeutic agent to a desired target within an organism, such as a human. The new compositions and methods can also be used to deter ethanol consumption and to treat glutamate-related disorders. Accordingly, the invention provides compositions and methods to prepare the compositions. Also provided are methods to detect compounds provided by the invention.

In accordance with the present invention, novel compounds which demonstrate useful biological activity, and that are particularly useful for treating glutamate-related disorders, are provided.

The present invention provides a compound of Formula (I):

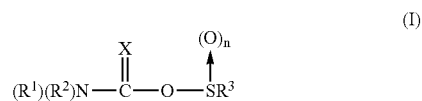

wherein:

a) $R^1$ and $R^2$ are individually H, $(C_1-C_8)$alkyl, aryl, heteroaryl, D or -L-D; and $R^3$ is $(C_1-C_8)$alkyl, aryl, heteroaryl, or a glutathione derivative; or b) $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$, which ring is optionally substituted with one or more D or -L-D; and $R^3$ is $(C_1-C_8)$alkyl, aryl, heteroaryl, or a glutathione derivative; or c) $R^1$ and $R^3$ together are a divalent ethylene or propylene chain and $R^2$ is H, $(C_1-C_8)$alkyl, aryl, heteroaryl, D or -L-D; or d) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene (—$CH_2$—), ethylene (—$CH_2CH_2$—), or a direct bond; and wherein the ring comprising $R_b$ and $R^3$ is a five- or six-membered ring; or e) $R^1R^2N$ taken together are D; $R^3$ is $(C_1-C_8)$alkyl, aryl, heteroaryl, or a glutathione derivative; and X is O or S; and n is 0, 1, or 2; and each D is independently a therapeutic agent; and each L is independently a linking agent; and each $R_a$ is absent or is hydrogen, $(C_1-C_8)$alkyl, $(C_1-C_8)$alkanoyl, phenyl, benzyl, or phenethyl;

wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;

or a pharmaceutically acceptable salt thereof.

In another aspect, the present invention also provides:

a pharmaceutical composition comprising a therapeutically effective amount of a compound of Formula (I) or a pharmaceutically acceptable salt thereof; and a pharmaceutically acceptable carrier (the composition preferably comprises a therapeutically effective amount of the compound or salt);

a method for treatment of a glutamate-related disease in a mammal treatable by administration of a compound of Formula (I) comprising administering to the mammal a therapeutically effective amount of a compound of Formula (I), or a pharmaceutically acceptable salt thereof;

a method to deter ethanol consumption by a human comprising administering to the human a compound of Formula (I), or a pharmaceutically acceptable salt thereof;

a method for preparing a compound of Formula (I) where $R^1$, $R^2$, $R^3$, X and n have any of the values described herein comprising contacting a corresponding compound of Formula (II)

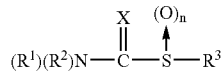

wherein n is 1 or 2 with silica gel; and a method to increase the effectiveness of a therapeutic agent comprising linking the therapeutic agent to a compound of Formula (I).

The invention also provides a compound of Formula (II):

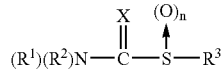

wherein:

a) $R^1$ and $R^2$ are individually H, $(C_1-C_8)$alkyl, aryl, heteroaryl, D, -L-D, or $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$; or b) $R^1$ and $R^3$ together are a divalent ethylene or propylene chain and $R^2$ is $(C_1-C_8)$alkyl, aryl, heteroaryl, D or -L-D; or c) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$;

wherein $R_b$ and $R^3$ taken together are methylene (—$CH_2$—), ethylene (—$CH_2CH_2$—), or a direct bond; and wherein the ring comprising $R_b$ and $R^3$ is a five- or six-membered ring; or d) $R^1R^2N$ taken together are D; and $R^3$ is $(C_1-C_8)$alkyl, aryl, heteroaryl, or a glutathione derivative; and e) $R^1$ and $R^2$ are independently D; $R^3$ is $(C_1-C_8)$alkyl, aryl, heteroaryl, or a glutathione derivative; or f) $R^1$ and $R^2$ are independently -L-D; or $R^3$ is $(C_1-C_8)$ alkyl, aryl, heteroaryl, or a glutathione derivative; and X is O or S; and n is 0, 1, or 2; and each D is independently a therapeutic agent; and each L is independently a linking group;

each $R_a$ is absent or is hydrogen, $(C_1-C_8)$alkyl, $(C_1-C_8)$ alkanoyl, phenyl, benzyl, or phenethyl; and $R^3$ is hydrogen, $(C_1-C_8)$alkyl, aryl, heteroaryl, or a glutathione derivative;

or a pharmaceutically acceptable salt thereof;

wherein any aryl or heteroaryl in $R^1$, $R^2$, or $R^3$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, and carboxy;

wherein the compound of Formula (II) or the salt thereof is essentially free of a compound of Formula (I) as described herein.

In another aspect, the present invention also provides:

a pharmaceutical composition comprising a therapeutically effective amount of a compound of Formula (II) or a pharmaceutically acceptable salt thereof; and a pharmaceutically acceptable carrier (the composition preferably comprises a therapeutically effective amount of the compound or salt);

a method for treatment of a glutamate-related disease in a mammal treatable by administration of a compound of Formula (II) comprising administering to the mammal a therapeutically effective amount of a compound of Formula (II), or a pharmaceutically acceptable salt thereof;

a method to deter ethanol consumption by a human comprising administering to the human a compound of Formula (II), or a pharmaceutically acceptable salt thereof;

a method for preparing a compound of Formula (II) wherein n is 1 or 2, comprising reacting a corresponding compound $R^1R^2$—N—C(=O)—S—$R^3$ wherein n=0 with hydrogen peroxide; and a method to increase the effectiveness of a therapeutic agent comprising linking the therapeutic agent to a compound of Formula (II).

The invention also provides a compound of Formula (II):

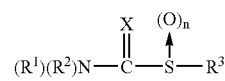

wherein:

a) $R^1$ is D or -L-D; $R^2$ is H, $(C_1-C_8)$alkyl, aryl, heteroaryl, D or -L-D; and $R^3$ is $(C_1-C_8)$alkyl, aryl, heteroaryl, or a glutathione derivative; or b) $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$, which ring is substituted with one or more D or -L-D; and $R^3$ is $(C_1-C_8)$alkyl, aryl, heteroaryl, or a glutathione derivative; or c) $R^1$ and $R^3$ are a divalent ethylene or propylene chain and $R^2$ is D or -L-D; or d) $R^1R^2N$ taken together are D; and $R^3$ is $(C_1-C_8)$alkyl, aryl, heteroaryl, or a glutathione derivative; or X is O or S; and n is 0, 1, or 2;

each D is independently a therapeutic agent; and each L is independently a linking group;

each $R_a$ is absent or is hydrogen, $(C_1-C_8)$alkyl, $(C_1-C_8)$ alkanoyl, phenyl, benzyl, or phenethyl;

wherein any aryl or heteroaryl of $R^2$ and $R^3$ may optionally be substituted with 1, 2, or 3 substituents independently selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, carboxy, D and -L-D;

or a pharmaceutically acceptable salt thereof.

In another aspect, the present invention also provides:

a pharmaceutical composition comprising a therapeutically effective amount of such a compound of Formula (II) or a pharmaceutically acceptable salt thereof; and a pharmaceutically acceptable carrier (the composition preferably comprises a therapeutically effective amount of the compound or salt);

a method for treatment of a glutamate-related disease in a mammal treatable by administration of such a compound of Formula (II) comprising administering to the mammal a therapeutically effective amount of a compound of Formula (II), or a pharmaceutically acceptable salt thereof;

a method to deter ethanol consumption by a human comprising administering to the human such a compound of Formula (II), or a pharmaceutically acceptable salt thereof;

a method for preparing a compound of Formula (II) wherein n is 1 or 2, comprising reacting a corresponding compound comprising —N—C(=O)—S— with hydrogen peroxide; and a method to increase the effectiveness of a therapeutic agent (D) comprising linking the therapeutic agent to the remainder of a compound of Formula (II).

The invention also provides a compound of Formula (III):

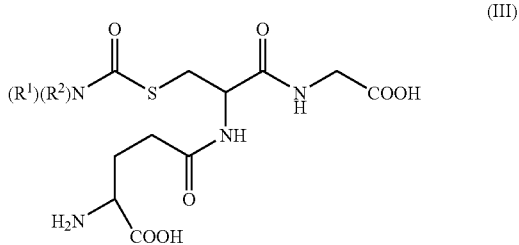

wherein:

a) $R^1$ and $R^2$ are individually H, $(C_1-C_8)$alkyl, aryl, heteroaryl, D or -L-D; or b) $R^1$ is D or -L-D; $R^2$ is H, $(C_1-C_8)$alkyl, aryl, heteroaryl, D or -L-D; or c) $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$; which ring is optionally substituted with one or more D or -L-D; or d) $R^1$ and $R^2$ together with the nitrogen to which they are attached are an azetidino, pyrrolidino, piperidino, hexamethyleneimin-1-yl, or heptamethylene-imin-1-yl ring;

wherein any aryl or heteroaryl in $R^1$ or $R^2$ may optionally be substituted with 1, 2, or 3 substituents selected from the group consisting of halo, nitro, cyano, hydroxy, $(C_1-C_8)$alkoxy, $(C_1-C_8)$alkanoyl, $(C_2-C_8)$alkanoyloxy, trifluoromethyl, trifluoromethoxy, carboxy, D and -L-D; or e) $R^1R^2N$ taken together are D; and each D is independently a therapeutic agent; and each L is independently a linking group; and each $R_a$ is absent or is hydrogen, $(C_1-C_8)$alkyl, $(C_1-C_8)$alkanoyl, phenyl, benzyl, or phenethyl;

or a pharmaceutically acceptable salt thereof;

wherein $R^1$ and $R^2$ are not both ethyl.

In a preferred embodiment of a compound of Formula (III), $R^1$ and $R^2$ are not ethyl.

In another preferred embodiment of a compound of Formula (III), $R^1$ and $R^2$ are not alkyl.

In another preferred embodiment of a compound of Formula (III), $R^1$ and $R^2$ are not H, $(C_1-C_8)$alkyl, aryl, heteroaryl.

In another aspect, the present invention provides:

a pharmaceutical composition comprising a therapeutically effective amount of such a compound of Formula (III) or a pharmaceutically acceptable salt thereof; and a pharmaceutically acceptable carrier (the composition preferably comprises a therapeutically effective amount of the compound or salt);

a method for treatment of a glutamate-related disease in a mammal treatable by administration of such a compound of Formula (III) comprising administering to the mammal a therapeutically effective amount of a compound of Formula (III), or a pharmaceutically acceptable salt thereof;

a method to deter ethanol consumption by a human comprising administering to the human such a compound of Formula (III), or a pharmaceutically acceptable salt thereof;

a method for preparing such a compound of Formula (III) comprising reacting a corresponding compound of Formula (II) wherein n is 2 and X is O with glutathione; and a method to increase the effectiveness of a therapeutic agent comprising linking the therapeutic agent to a compound of Formula (III).

The invention also provides a method to conjugate glutathione to a compound that comprises the group —N—C(=O)—O—S(O)$_n$— where n is 0, 1 or 2; or to a compound that comprises the group —N—C(=O)—S(O)$_n$— where n is 2, comprising reacting the compound with glutathione to form a glutathione conjugate;

a method for preparing a compound comprising the group —N—C(=O)—S(O)—, comprising reacting a corresponding compound comprising the group —N—C(=O)—S— with hydrogen peroxide;

a method for preparing a compound comprising the group —N—C(=O)—S(O)$_2$— comprising, reacting a corresponding compound comprising the group —N—C(=O)—S— or the group —N—C(=O)—S(O)— with a peracid, such as m-chloroperbenzoic acid; and a method to determine if a sample contains a compound comprising the group —N—C(=O)—O—S(O)$_n$— wherein n is 0, 1 or 2 comprising contacting the sample with a suitable thiol, such as thionitrobenzoate; and detecting if a reaction product is formed by the reaction of the compound with the suitable thiol.

The invention also provides a method for treating cocaine addiction, Alzheimer's disease, ischemia, stroke, opioid addiction, Creutzfeldt-Jakob disease, noise-induced hearing loss, hepatic encephalopathy, cyanide-induced apoptosis, diabetic neuropathy, schizophrenia, amphetamine addiction, non-ketonic hyperglycinemia or bipolar disorder in a mammal comprising administering an effective amount of a compound of Formula (II)

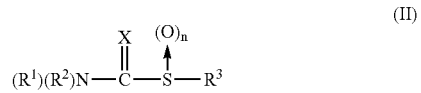

wherein:

a) $R^1$ and $R^2$ are individually H, $(C_1-C_8)$alkyl, aryl, heteroaryl, or $R^1$ and $R^2$ together with the nitrogen to which they are attached are a 4–8 membered ring optionally comprising 1, 2, or 3 additional heteroatoms selected from the group consisting of non-peroxide oxygen, sulfur, and $N(R_a)$, wherein each $R_a$ is absent or is hydrogen, $(C_1-C_8)$alkyl, $(C_1-C_8)$alkanoyl, phenyl, benzyl, or phenethyl; and $R^3$ is $(C_1-C_8)$alkyl, aryl, heteroaryl, or a glutathione derivative; or b) $R^1$ and $R^3$ together are a divalent ethylene or propylene chain and $R^2$ is $(C_1-C_8)$alkyl, aryl, or heteroaryl; or c) $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$;

wherein $R_b$ and $R^3$ taken together are methylene (—CH$_2$—), ethylene (—CH$_2$CH$_2$—), or a direct bond; and wherein the ring comprising $R_b$ and $R^3$ is a five- or six-membered ring;

wherein any aryl or heteroaryl in $R^1$, $R^2$, or $R^3$ may optionally be substituted with 1, 2, or 3 substituents selected from the group consisting of halo, nitro, cyano, hydroxy, (C$_1$–C$_8$)alkoxy, (C$_1$–C$_8$)alkanoyl, (C$_2$–C$_8$)alkanoyloxy, trifluoromethyl, trifluoromethoxy, and carboxy;

X is O or S; and n is 0, 1, or 2;

or a pharmaceutically acceptable salt thereof.

DETAILED DESCRIPTION OF THE INVENTION

Figure 1:
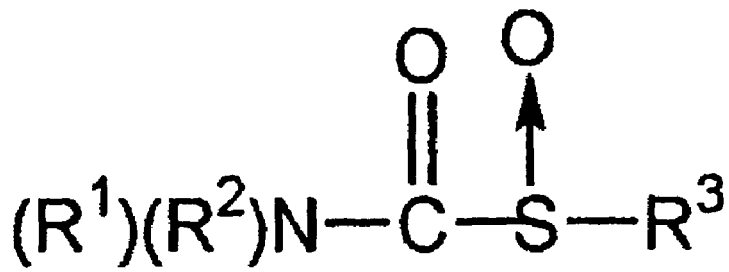
FIG. 1 depicts the rearrangement of a carbamoyl thioester sulfoxide (Formula (II), n=1) to a carbamoyl sulfenate (Formula (I), n=0).
Figure 1:
Figure 1:
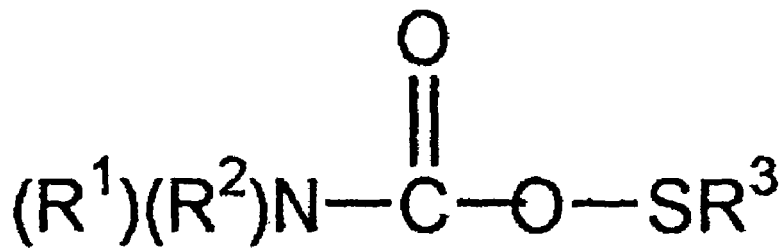

Disulfiram has been used in the treatment of alcoholism for more than 50 years (J. Hald et al., *Lancet*, 2:1001 (1948); M. D. Faiman, *Biochemistry and Pharmacology of Ethanol*, Vol. 2., eds. Majchrowicz, E. and Novel, E. P., pp. 325–348, Plenum Press, New York). It has recently been demonstrated that disulfiram exerts its anti-alcohol effect in vivo only after bioactivation to the active metabolite S-methyl-N,N-diethylthiolcarbamate sulfoxide (DETC-MeSO) (A. Madan et al., *Drug Metab. Dispos.*, 23:1153 (1995)). It has been reported that DETC-MeSO is a potent and selective carbamoylating agent for sulfhydryl groups (L. Jin et al., *Chem. Res. Toxicol.*, 7:526 (1994)). However, it is demonstrated herein that, although DETC-MeSO is a potent inactivator of the mitochondrial aldehyde dehydrogenase, it does not react with sulfhydryl groups. By contrast, the previously reported effect of DETC-MeSO on brain glutamate receptors (Faiman et al. (2000), U.S. Pat. No. 6,156,794; Ningaraj et al., *J. Biomed. Sci.*, 8:104 (2001)), with concomitant neuroprotective effects, is a consequence of either DETC-MeSO or its isomer S-methyl-O-(N,N-diethylcarbamoyl)sulfenate (DECOSMe). The neuroprotective effects depend on oxidation of DETC-MeSO to a sulfone (DETC-MeSO$_2$) in vivo, followed by reaction of DETC-MeSO$_2$ with glutathione to form S-(N,N-diethylcarbamoyl)glutathione (carbamathione) or direct reaction of DECOSMe with glutathione to form carbamathione. In either case (DETC-MeSO or DECOSMe) the neuroprotective effects are dependent on the formation of carbamathione and the interaction of carbamathione with brain glutamate receptors. The previously reported reaction of DETC-MeSO with sulfhydryl groups was due to the presence of the isomer DECOSMe, which does react with sulfhydryl groups, in the mixture.

The neuroprotective effect of carbamathione augments the direct alcohol aversive effect of DETC-MeSO. Carbamathione will "down regulate" glutamate receptors of the NMDA subtype, which are "up regulated" by chronic alcohol consumption. Carbamathione will prevent ethanol-induced kindling seizures or the convulsions that are obtained during withdrawal from chronic alcohol consumption (Ningaraj et al., *J. Biomed. Sci.*, 8:104 (2001)). Thus DETC-MeSO has two therapeutic effects in the treatment of alcohol abuse, one aversive by inhibition of aldehyde dehydrogenase and the other restorative by reversing the NMDA (glutamate) receptor effect associated with chronic ethanol consumption. The former is a direct effect of DETC-MeSO on the patient's ability to metabolize alcohol, while the latter effect is mediated by carbamathione. By contrast, disulfiram is known to produce a number of unwanted neurological side-effects.

Few, perhaps none, of the adverse neurological effects of disulfiram can be attributed to modification of glutamate receptors. Disulfiram is metabolized to carbon disulfide, a known neurotoxin, and potently inhibits copper enzymes, such as superoxide dismutase and dopamine β-hydroxylase, through the action of another disulfiram metabolite, diethyldithiocarbamate (T. J. Haley, *Drug Metab. Rev.*, 9:319 (1979); E. I. Eneanya et al., *Ann. Rev. Pharmacol. Toxicol.*, 21:575 (1981)).

DETC-MeSO, DECOSMe, and carbamathione do not share any of these latter effects with disulfiram, such as carbon disulfide formation or copper-enzyme inhibition, so they would be expected to more selectively affect glutamate receptors in vivo. In particular, DETC-MeSO, DECOSMe, and carbamathione are not likely to cause the seizures, optic neuritis and peripheral neuropathy linked to higher doses (>500 mg/day) of disulfiram, that are most probably a consequence of CS$_2$ formation (C. M. Fisher, *Arch. Neurol.*, 46:798 (1989); B. Mokri et al., *Neurology*, 31:73 (1981); H. R. Hotson et al., *Arch. Neurol.*, 33:141 (1976)).

Figure 2:
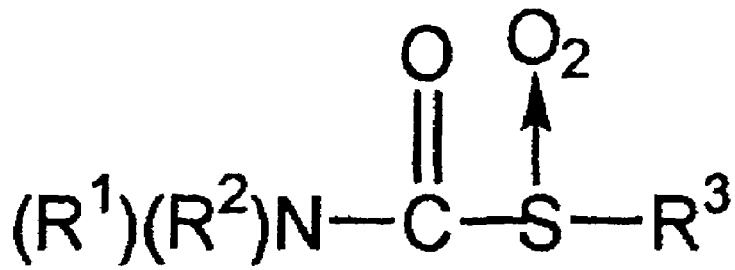
FIG. 2 illustrates the rearrangement of a carbamoyl thioester sulfone (Formula (II), n=2) to a carbamoyl sulfinate (Formula (I), n=1).
Figure 2:
Figure 2:
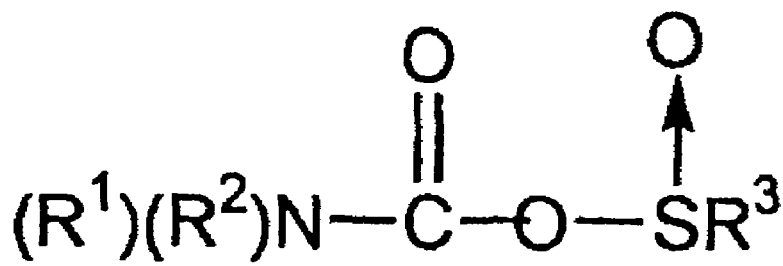
Figure 3:
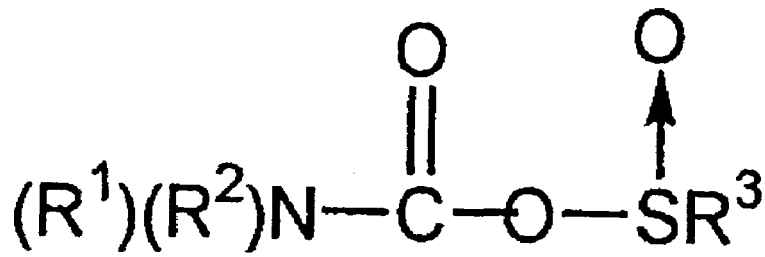
FIG. 3 illustrates the oxidation of a carbamoyl sulfinate (Formula (I), n=1) to a carbamoyl sulfonate (Formula (I), n=2).
Figure 3:
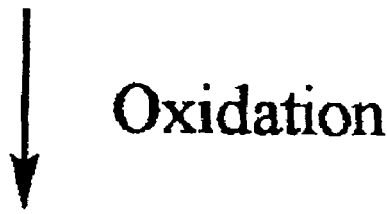
Figure 3:
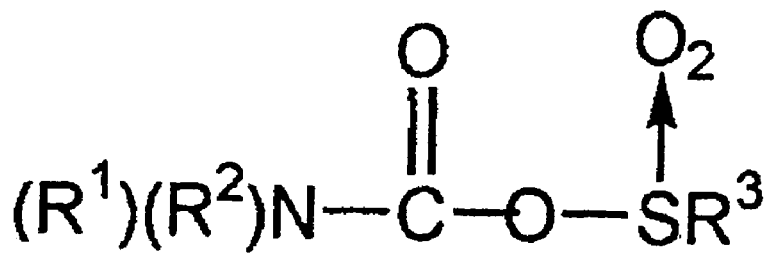
Figure 4:
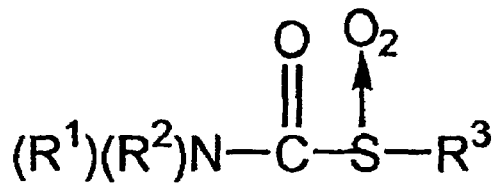
FIG. 4 illustrates the carbamoylation of glutathione by a carbamoyl thioester sulfone (Formula (II), n=2) to form an S-carbamoyl glutathione (Formula (III)) and a sulfinate.
Figure 4:
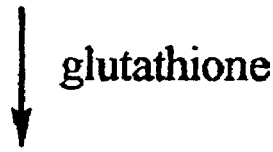
Figure 4:
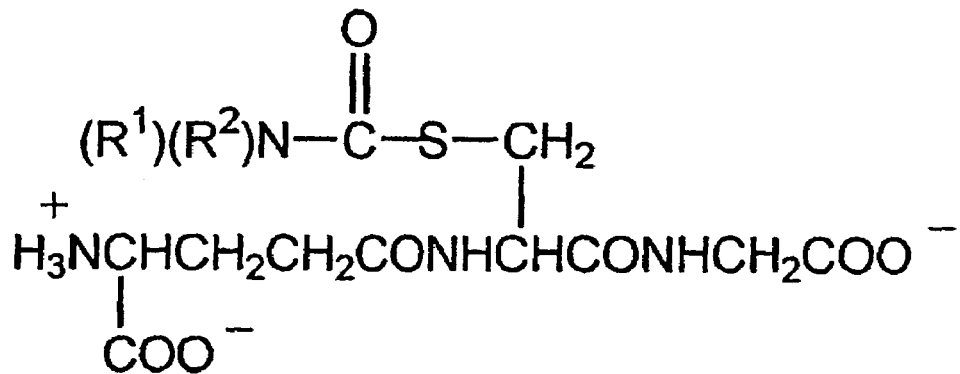

As described herein, when oxidized to sulfoxides or sulfones, carbamoyl thioesters rearrange to carbamoyl sulfenates (FIG. 1) or carbamoyl sulfinates (FIG. 2), respectively. Oxidation of carbamoyl sulfinates would give carbamoyl sulfonates, as illustrated in FIG. 3. Thus, there are three possible oxidation states for carbamoyl esters that are attached to an oxygen-sulfur moiety: (1) carbamoyl sulfenates (FIG. 1), (2) carbamoyl sulfinates (FIG. 2), and (3) carbamoyl sulfonates (FIG. 3). These three carbamoyl esters can affect the use of carbamoyl thioesters as therapeutic agents or as synthetic intermediates. Thus, synthetic methods are disclosed herein that manage the extent of these rearrangements for oxidized carbamoyl thioesters (sulfoxides and sulfones).

Definitions

The term "essentially free" as used in reference to a compound of Formula (II) means a preparation of a compound of Formula (II) having less than 10%, 5%, 1% or 0.5% by weight of a compound of Formula (I). The amount of a compound of Formula (I) may be measured by loss of absorbance at an appropriate wavelength, such as 412 nm, due to reaction of a chromophoric thiol, such as 5-thio-2-nitrobenzoate, with the compound of Formula (I) when incubated under anaerobic conditions as described in Example 8 herein.

The term "glutamate related disease" includes, but is not limited to, neurodegenerative diseases associated with elevated levels of extracellular glutamate, including Huntington's disease, Alzheimer's disease, Parkinson's disease, acquired immunodeficiency syndrome (AIDS) neuropathy, epilepsy, nicotine addiction, cerebral ischemia (stroke), and familial Amyotrophic Lateral Sclerosis (ALS); as well as neurodegenerative diseases associated with thiamine deficiency, such as Wernicke-Korsakoff syndrome, cerebral beriberi, Machado-Joseph disease, Soshin disease, and related diseases. Such diseases are disclosed by Thomas et al., *J. Am. Geriatr. Soc.*, 43:1279 (1995) and U.S. Pat. No. 6,156,794. Glutamate-related diseases also include diseases or conditions wherein glutamate related activity is implicated, such as anxiety, glutamate related convulsions, hepatic encephalopathy, neuropathic pain, domoic acid poisoning, hypoxia, anoxia, mechanical trauma to the nervous system, hypertension, alcohol withdrawal seizures, alcohol addiction, alcohol craving, cardiovascular ischemia, oxygen convulsions, and hypoglycemia. Other disorders which have been linked to excess or aberrant activation of glutamate receptors include Creutzfeldt-Jakob disease (Muller et al., *Mech. Ageing. Dev.*, 116:193 (2000)), cocaine addiction (Ciano & Everitt, *Neuropsychopharmacology*, 25:341 (2001); Gregy, *Crit. Rev. Neurobiol.*, 14:91 (2000)), noise-induced hearing loss (Chen et al., *Hear. Res.*, 154:108 (2001); Oestreicher et al., *Acta Otolaryngol*, 119:174 (1999); Jager et al., *Exp. Brain Res.*, 134:426 (2000); Pujol & Puel, Ann. NY *Acad. Sci.*, 884:249 (1999)), heroin addiction and addiction to other opioids (Bisaga et al., *Psychopharmacology* (Bert), 157:1 (2001); Bespalov et al., *Neurosci. Biobehav. Rev.*, 25:343 (2001)), amphetamine addiction (Gregy, *Crit. Rev. Neurobiol.*, 14:91 (2000); Sripada et al., *Brain Res. Brain Res. Rev.*, 35:97 (2001)), cyanide-induced apoptosis (Jensen et al., *Toxicol. Sci.*, 58:127 (2000)), schizophrenia (Bird et al., *Psychopharmacology* (Bert), 155:299 (2001)), bipolar disorder (Dean et al., *J. Affect. Disord.*, 66:147 (2001)), peripheral neuropathy associated with diabetes (Kosenko et al., *Vopr. Med. Khim.*, 45:304 (1999); Elgado-Esteban et al., *J. Neurochem*, 75:1618 (2000); Li et al., Brain Res., 849:34 (1999)) and nonketonic hyperglycinemia (Deutsch et al., Clin. *Neuropharmacol.*, 21:71(1998)).

Glutamate-related diseases also include all diseases associated with excess activity of the neuronal form of nitric oxide synthase (nNOS), since the nNOS is physically associated with glutamate receptors of the NMDA subtype and is activated by this type of glutamate receptor (Putzke et al., *Brain Res. Mol. Brain Res.*, 85:13 (2000)).

The term "linker" refers to a divalent organic group that links a therapeutic agent to a compound of Formula (I), Formula (II) or Formula (III). The term "linking group" does not, however, extend to cover solid inert supports such as beads, glass particles, fibers, and the like. The nature of the linking group is not critical, provided the compound comprising the linking group has suitable chemical and biological properties to be administered within a pharmaceutical composition. For example, the compound should be capable of traversing the blood-brain barrier. Certain glutathione conjugates are readily transported across the blood-brain barrier to the central nervous system (Faiman et al., 2000; U.S. Pat. No. 6,156,794). Preferably the linking group is of low molecular weight. Typically, a linking group separates the therapeutic agent from the compound of Formula (I), Formula (II) or Formula (III) by about 2 to about 20 Ångstroms, or preferably by about 2 to about 10 Ångstroms. Suitable linking groups include divalent alkylene, e.g. —$(CH_2)_{1-8}$—, alkenylene, and alkynylene chains. In addition, the linker can incorporate ether or thioether groups within the chain; the linking group can also be linked to the therapeutic agent or to the compound of Formula (I), Formula (II) or Formula (III) through ether, ester, amide or thioether groups.

A "pharmaceutical composition" includes a compound of the invention, for example a compound of Formula (I), (II) or (III), in combination with a pharmaceutically acceptable carrier. Examples of acceptable carriers include a solid, gelled or liquid diluent or an ingestible capsule. One or more of the compounds of the invention, the salts thereof, or a mixture thereof, may be administered orally in the form of a pharmaceutical unit dosage form comprising the compound in combination with a pharmaceutically acceptable carrier. A unit dosage to the compound or its salt may also be administered without a carrier material. The pharmaceutical compositions of the invention may be prepared in many forms that include tablets, hard or soft gelatin capsules, aqueous solutions, suspensions, and liposomes and other slow-release formulations, such as shaped polymeric gels.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dosage form in ampules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the compound of the invention may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506; and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The compounds can also be delivered via iontophoresis, e.g., as disclosed in U.S. Pat. Nos. 4,140,122; 4,383,529; or 4,051,842.

Pharmaceutical compositions suitable for topical administration in the mouth include unit dosage forms such as lozenges comprising a compound of the invention in a flavored base, usually sucrose and acadia or tragacanth; pastilles comprising the compound in an inert base such as gelatin and glycerin or sucrose and acacia; mucoadherent gels, and mouthwashes comprising the compound in a suitable liquid carrier.

When desired, the above-described pharmaceutical compositions can be adapted to give sustained release of the compound employed, e.g., by combination with certain hydrophilic polymer matrices, e.g., comprising natural gels, synthetic polymer gels or mixtures thereof.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Pharmaceutical compositions suitable for vaginal administration may be presented as pessaries, tampons, creams, gels, pastes, foams or sprays containing, in addition to the composition of the invention.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds of the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (isoproterenol inhaler—Wintrop) and the Medihaler® (isoproterenol inhaler—Riker).

For topical administration to the eye, the compounds can be administered as drops, gels (S. Chrai et al., U.S. Pat. No. 4,255,415), gums (S. L. Lin et al., U.S. Pat. No. 4,136,177) or via a prolonged-release ocular insert (A. S. Michaels, U.S. Pat. No. 3,867,519 and H. M. Haddad et al., U.S. Pat. No. 3,870,791).

Pharmaceutical compositions of the invention may also contain other adjuvants such as flavorings, colorings, antimicrobial agents, or preservatives.

It will be further appreciated that the amount of the present compound(s), a combination of the present compounds, or an active salt or derivative thereof, required for use in treatment will vary not only with the particular salt selected but also with the route of administration, the nature of the condition being treated and the age and condition of the patient and will be ultimately at the discretion of the attendant physician or clinician.

The amount of a compound of the invention or a combination thereof that is administered and the frequency of administration to a given human patient will depend upon a variety of variables related to the patient's psychological profile and physical condition. For evaluations of these factors, see J. F. Brien et al., *Europ. J. Clin. Pharmacol.*, 14, 133 (1978); and *Physicians' Desk Reference*, Charles E. Baker, Jr., Pub., *Medical Economics Co.*, Oradell, N.J. (41st ed., 1987). Generally, the dosages of the present compounds will be smaller than that administered in the case of disulfiram which is presently administered at 4–8 mg/kg orally, or than putative dosages of DETC-Me. All percentages are weight percentages unless otherwise indicated.

"Pharmaceutically acceptable salts" of the compounds of the invention include, but are not limited to, the nontoxic addition salts with organic and inorganic acids, such as the citrates, bicarbonates, malonates, tartrates, gluconates, hydrochlorides, sulfates, phosphates, and the like.

A "therapeutic agent" is a substance that may be used in the diagnosis, cure, mitigation, treatment, or prevention of disease in a human or another animal. Such therapeutic agents are recognized in the official United States Pharmacopeia, official Homeopathic Pharmacopeia of the United States, official National Formulary or any supplement thereof.

Therapeutic agents that can be linked to the compounds of the invention include nucleoside analogs, urinary tract agents, vaginal agents, and vasodilators neurodegenerative agents (e.g, Parkinson's disease), obesity agents, ophthalmic agents, osteoporosis agents, parasympatholytics, parasympathommetics, anti-anesthetics, prostaglandins, psychotherapeutic agents, respiratory agents, sedatives, hypnotics, skin and mucous membrane agents, anti-bacterials, anti-fungals, anti-neoplastics, cardioprotective agents, cardiovascular agents, anti-thrombotics, central nervous system stimulants, cholinesterase inhibitors, contraceptives, deodorants, dopamine receptor agonists, erectile dysfunction agents, fertility agents, gastrointestinal agents, gout agents, hormones, immunomodulators, suitably functionalized analgesics or general or local anesthetics, anti-convulsants, anti-diabetic agents, anti-fibrotic agents, anti-infectives, motion sickness agents, muscle relaxants, immunosuppressives, migraine agents, non-steriodal anti-inflammatory drugs (NSAIDs), smoking cessation agents, or sympatholytics (see Physicians' Desk Reference, 55 ed., 2001, Medical Economics Company, Inc., Montvale, N.J., pages 201–202).

Examples of specific therapeutic agents that can be linked to the compounds of the invention are flomoxef; fortimicin(s); gentamicin(s); glucosulfone solasulfone; gramicidin S; gramicidin(s); grepafloxacin; guamecycline; hetacillin; isepamicin; josamycin; kanamycin(s); flomoxef; fortimicin(s); gentamicin(s); glucosulfone solasulfone; gramicidin S; gramicidin(s); grepafloxacin; guamecycline; hetacillin; isepamicin; josamycin; kanamycin(s); bacitracin; bambermycin(s); biapenem; brodimoprim; butirosin; capreomycin; carbenicillin; carbomycin; carumonam; cefadroxil; cefamandole; cefatrizine; cefbuperazone; cefclidin; cefdinir; cefditoren; cefepime; cefetamet; cefixime; cefmenoxime; cefminox; cladribine; apalcillin; apicycline; apramycin; arbekacin; aspoxicillin; azidamfenicol; aztreonam; cefodizime; cefonicid; cefoperazone; ceforanide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; 6-mercaptopurine; thioguanine; capecitabine; docetaxel; etoposide; gemcitabine; topotecan; vinorelbine; vincristine; vinblastine; teniposide; melphalan; methotrexate; 2-p-sulfanilyanilinoethanol; 4,4'-sulfinyl-dianiline; 4-sulfanilamidosalicylic acid; butorphanol; nalbuphine. streptozocin; doxorubicin; daunorubicin; plicamycin; idarubicin; mitomycin C; pentostatin; mitoxantrone; cytarabine; fludarabine phosphate; butorphanol; nalbuphine. streptozocin; doxorubicin; daunorubicin; plicamycin; idarubicin; mitomycin C; pentostatin; mitoxantrone; cytarabine; fludarabine phosphate; acediasulfone; acetosulfone; amikacin; amphotericin B; ampicillin; atorvastatin; enalapril; ranitidine; ciprofloxacin; pravastatin; clarithromycin; cyclosporin; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; floxuridine; dirithromycin; doxycycline; enoxacin; enviomycin; epicillin; erythromycin; leucomycin(s); lincomycin; lomefloxacin; lucensomycin; lymecycline; meclocycline; meropenem; methacycline; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton; ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepartricin; nystatin; oligomycin(s); perimycin A; tubercidin; 6-azauridine; 6-diazo-5-oxo-L-norleucine; aclacinomycin(s); ancitabine; anthramycin; azacitadine; azaserine; bleomycin(s); ethyl biscoumacetate; ethylidene dicoumarol; iloprost; lamifiban; taprostene; tioclomarol; tirofiban; amiprilose; bucillamine; gusperimus; gentisic acid; glucamethacin; glycol salicylate; meclofenamic acid; mefenamic acid; mesalamine; niflumic acid; olsalazine; oxaceprol; S-enosylmethionine; salicylic acid; salsalate; sulfasalazine; tolfenamic acid; carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; Tomudex® (N-[[5-[[(1,4-Dihydro-2-methyl-4-oxo-6-quinazolinyl)methyl]methylamino]-2-thienyl]carbonyl]-L-glutamic acid), trimetrexate, tubercidin, ubenimex, vindesine, zorubicin; argatroban; coumetarol or dicoumarol.

Lists of additional therapeutic agents can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J.

A "thiol-reactive" substance is a substance that reacts with a component having a thiol-group (e.g. thionitrobenzoate) to form a detectable product. Such thiol-reactive substances may be used to bind to and inactivate enzymes that contain reactive cysteine residues. Alternatively, such thiol-reactive compounds may be used to bind and conjugate with glutathione, such as in cases wherein modulation of oxidative stress is desired (e.g. regulation of arthritis or wound healing).

Halo is fluoro, chloro, bromo, or iodo. Alkyl includes both straight or branched-chain alkyl, as well as cycloalkyl and (cycloalkyl)alkyl. Aryl denotes a phenyl radical or an ortho fused bicyclic carbocyclic radical having about 6–12 carbon atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein each Y is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "glutathione derivative" means a group of the formula:

$H_2NCH(COOH)CH_2CH_2CONHCH(CH_2\sim)$
$CONHCH_2COOH$

Specific and preferred values listed below for radicals, substituents, and ranges, are for illustration only and they do not exclude other defined values or other values within defined ranges for the radicals and substituents.

Specifically, $(C_1-C_8)$alkyl can be methyl, ethyl, propyl, isopropyl, butyl, iso-butyl, sec-butyl, pentyl, 3-pentyl, hexyl, heptyl, octyl, cyclohexyl, $(C_1-C_8)$alkoxy can be methoxy, ethoxy, propoxy, isopropoxy, butoxy, iso-butoxy, sec-butoxy, pentoxy, isopropoxy, butoxy, iso-butoxy, sec-butoxy, pentoxy, 3-pentoxy, hexyloxy, heptyloxy, or octyloxy; $(C_1-C_8)$alkanoyl can be acetyl, propanoyl, butanoyl, isobutanoyl, pentanoyl, hexanoyl, heptanoyl, or octanoyl, and $(C_2-C_8)$alkanoyloxy can be acetoxy, propanoyloxy, butanoyloxy, isobutanoyloxy, pentanoyloxy, hexanoyloxy, heptanoyloxy, or octanoyloxy. Aryl can be phenyl, indenyl, or naphthyl. Heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thienyl, pyrimidinyl (or its N-oxide), indolyl, isoquinolyl (or its N-oxide) or quinolyl (or its N-oxide).

Preferably, alkyl is $(C_1-C_4)$alkyl and aryl is phenyl.

A specific group of compounds are compounds of Formula (I) or Formula (II) wherein $R^1$ and $R^2$ together with the nitrogen to which they are attached are a ring selected from the group consisting of azetidino, pyrrolidino, piperidino, hexamethyleneimin-1-yl, and heptamethyleneimin-1-yl. Another specific group of compounds are compounds of Formula (I) or (II) wherein $R^1$ and $R^3$ together are a divalent ethylene or propylene chain and $R^2$ is $(C_1-C_8)$alkyl, $(C_6-C_{12})$aryl, or heteroaryl. A third specific group of compounds are compounds of Formula (I) or (II) wherein $R^1$ and $R^2$ together with the nitrogen to which they are attached are an azetidino, pyrrolidino, piperidino, hexamethyleneimin-1-yl or heptamethyleneimin-1-yl ring, said ring being substituted on carbon by a substituent $R_b$; wherein $R_b$ and $R^3$ taken together are a divalent ethylene or propylene chain.

A preferred group of compounds are compounds of Formula (I) or Formula (II) wherein $R^1$ and $R^2$ are individually $(C_1-C_8)$alkyl, or $(C_6-C_{12})$aryl, hydrogen, or a glutathione derivative; X is O or S; n is 0, 1 or 2 or a pharmaceutically acceptable salt thereof.

Another preferred group of compounds are compounds of Formula (I) or Formula (II) wherein $R^3$ is aryl or heteroaryl and n is 0.

Another preferred group of compounds are compounds of Formula (III) wherein $R^1$ and $R^2$ are individually $(C_1-C_8)$ alkyl, or aryl; X is O; n is 0. When both $R^1$ and $R^2$ are ethyl ($C_2H_5$), this compound is referred to as carbamathione.

Another preferred group of compounds are compounds of Formula (III) wherein $R^1$ and $R^2$ are individually any therapeutic agent.

Another preferred group of compounds are compounds of Formula (III) wherein $R^1$ and $R^2$ are not ethyl.

Another preferred group of compounds are compounds of Formula (III) wherein $R^1$ and $R^2$ are not alkyl.

Another preferred group of compounds are compounds of Formula (III) wherein the therapeutic agent (D) is selected from the group consisting of neuroprotective agents, ophthalmic agents, psychotherapy agents, hypnotics, central nervous system stimulants, cholinesterase inhibitors, dopamine receptor agonists, dopamine receptor antagonists, antimigraine agents, antibiotic agents, antibacterial agents, anticancer agents, antifungal agents, antiparasitic agents, antiviral agents, amebicides, trichomonacides, analeptic agents, analgesics, anesthetics, anorexics, anthemintics, antiarthritics, antiasthma, antituberculosis agents, anti-cerebral edema agents, cholinergics, anticholinergics, anticoagulants, anticonvulsants, antidepressants, antidiabetic agents, antidiuretics, antifirinolytic agents, antihistamines, anti-inflammatory agents, antimalarials, antimetabolites, antineoplastics, anti-obesity agents, anti-parkinsonism agents, antipuritics, antipyretics, barbiturates, bronchial dilators, cardiovascular agents, antihyperlipemics, diuretics, hemostatics, immunosuppressive agents, ophthalmologicals, antiglaucomatous agents, mydriatics, cycloplegics, parasympathomimetics, parasympatholytic agents, psychostimulants, sedatives, sympatholytics, or sympathomimetics.

I. Compounds of Formula (I)

The invention provides compounds of Formula (I). These compounds may be used to treat glutamate-related diseases, such as those described herein. The compounds may also be conjugated with glutathione. Thus, the compounds of Formula (I) may be used as intermediates to associate a therapeutic agent that is linked to a compound of Formula (I) with glutathione. Such compounds are able to be used for directed delivery of a therapeutic agent to a desired location within the body of an organism, such as a human, particularly across the blood-brain barrier.

The invention also provides pharmaceutical compositions containing compounds of Formula (I). These pharmaceutical compositions may be formulated to suit any desired purpose. Examples of such formulations are disclosed herein.

The invention also provides methods for treating a glutamate-related disease by administration of an effective amount of a compound of Formula (I). The methods may involve administration of a compound of Formula (I) as described herein, alone, in a pharmaceutical composition, or in combination with other therapeutic agents and pharmaceutical compositions.

The invention also provides methods to deter ethanol consumption by administration of an effective amount of a compound of Formula (I) or a salt thereof, as described herein.

Also provided is a method for preparing a compound of Formula (I). The compounds of Formula (I), wherein n=0 or 1, are readily obtained by rearrangement of compounds of Formula (II), wherein n is one integer larger (i.e., n for compounds of Formula (II)=n for compounds of Formula (I)+1, one oxygen being incorporated into the carbamoyl linkage of Formula (I) compounds). The compounds of Formula (I), wherein n=2, may be prepared by oxidation of compounds of Formula (I), wherein n=1. Specific examples of reaction conditions and methods are disclosed in the examples contained herein.

The invention also provides methods to increase the effectiveness of a therapeutic agent by linking the therapeutic agent to a compound of Formula (I). The compounds and pharmaceutical compositions of Formula (I) may also be used to associate therapeutic agents with glutathione to increase the therapeutic efficiency of the therapeutic agent. Conjugation of glutathione to a compound of Formula (I) may be done in vitro, but it is preferable to use a compound of Fomula (II) to avoid the formation of oxidized glutathione as a side product (when n=0 for the compound of Formula (I)). The compound of Formula (I) may also be conjugated with glutathione in vivo through administration of the compound of Formula (I) to a subject in need thereof, wherein the compound will be conjugated with endogenous glutathione within the subject.

The compounds of Formula (I) are also useful synthetic intermediates for the association of therapeutic agents to glutathione (although compounds of Formula (II), n=2, are preferred due to concomitant oxidation of glutathione by compounds of Formula (I), n=0); these glutathione conjugates have utility in improving delivery of these therapeutic agents in humans or animals for greater therapeutic benefit.

II. Compounds of Formula (II)

The invention provides compounds of Formula (II). These compounds may be used to treat glutamate-related diseases, such as those described herein. The compounds may also be conjugated with glutathione. Thus, the compounds of Formula (II) may be used as intermediates to associate a therapeutic agent that is linked to a compound of Formula (II) with glutathione. Such compounds are able to be used for directed delivery of a therapeutic agent to a desired location within the body of an organism, particularly across the blood-brain barrier.

The invention also provides pharmaceutical compositions containing compounds of Formula (II). These pharmaceutical compositions may be formulated to suit any desired purpose. Examples of such formulations are disclosed herein.

The invention also provides methods for treating a glutamate-related disease by administration of an effective amount of a compound of Formula (II). The methods may involve administration of a compound of Formula (II) as described herein, alone, in a pharmaceutical composition, or in combination with other therapeutic agents and pharmaceutical compositions.

The invention also provides methods to deter ethanol consumption by administration of an effective amount of a compound of Formula (II) as described herein.

Also provided is a method for preparing a compound of Formula (II). The compounds of Formula (II), wherein n=1 or 2, may be prepared by oxidation of the corresponding thiol esters of Formula (IV):

$(R^1)(R^2)NC(=X)SR^3$     (IV)

wherein X, $R^1$, $R^2$, and $R^3$ are as described herein. Specific reaction conditions and compounds are provided (see Examples 1–11). The compounds of Formula (II) wherein n=1 or 2 can be separated from unreacted compounds through use of a suitable method, such as distillation.

Thiol esters of Formula (IV) wherein X=O and $R^1$ and $R^2$ are individually ($C_1$–$C_8$)alkyl, ($C_6$–$C_{12}$)aryl or heteroaryl; or wherein $R^1$ and $R^2$ together with the nitrogen to which they are attached are a 4–8 membered ring as described hereinabove, may be prepared by bubbling carbonylsulfide into a mixture of triethylamine and the requisite amine of formula $(R^1)(R^2)NH$, in a suitable solvent, such as t-butanol. In situ alkylation with the requisite iodide of Formula $R^3I$, yields the corresponding thiol ester of formula (IV). To prepare thiol esters of Formula (IV) in which $R^3$ is

glutathione is mixed with a carbamoyl ester of Formula (I) in which n=0, 1 or 2, a thiol ester of Formula (II) in which n=2, or a mixture of thiol esters of Formula (I) and Formula (II) of this description in a suitable solvent, such as water, and with 2 equivalents of a suitable base, such as lithium bicarbonate. A thiol ester of Formula (I) in which n=0 is not preferred since oxidation of glutathione will take place and require chromatographic purification of the product or further processing of the reaction product. A thiol ester of Formula (II) in which n=0 or 1 should not be used since the reaction will not take place. Following completion of the reaction the product can be collected by crystallization by addition of a suitable water-miscible solvent, such as ethanol.

Dithiocarbamates of Formula (IV) (X=S) can be prepared using techniques that are well known in the art, for example, as disclosed by M. Faiman et al., *Alcoholism*, 7, 307 (1983). The final products can be purified by chromatography on silica gel. Useful synthetic methods are also disclosed in U.S. Pat. No. 5,035,878, issued Jul. 30, 1991.

Compounds of Formula (II), wherein $R^1$ and $R^3$ together are a divalent ethylene or propylene chain and $R^2$ is ($C_1$–$C_8$) alkyl, ($C_6$–$C_{12}$)aryl, or heteroaryl; or compounds of Formula (I) wherein $R^1$ and $R^2$ together with the nitrogen to which they are attached are an azetidino, pyrrolidino, piperidino, hexamethyleneimin-1-yl, or heptamethylene-imin-1-yl ring, said ring being substituted on carbon by a substituent $R_b$; wherein $R_b$ and $R^3$ taken together are methylene (—$CH_2$—), ethylene (—$CH_2CH_2$—), or a direct bond; and wherein the ring comprising $R_b$ and $R^3$ is a five- or six-membered ring; can be prepared by condensing carbonyl chloride with the requisite precursor comprising an amine and a mercaptan. Conversion of the carbamoyl thioester to a sulfoxide can be carried out using techniques that are well known in the art for example, as disclosed by M. Faiman et al., *Alcholism*, 7, 307 (1983). Conversion of a portion of these sulfoxides (Formula (II)) to carbamoyl sulfenates (Formula (I)) will occur spontaneously (i.e., migration of the carbamoyl moiety from sulfur to oxygen). Exposure of the sulfoxides to silica gel will accelerate their rate of conversion to sulfenates. The relative composition of the mixture of sulfoxide and sulfenate at equilibrium will depend on the nature of the substituents.

The invention also provides a method for preparing a compound of Formula (II) that is essentially free of a compound of Formula (I). The method generally involves oxidation of thiol esters of Formula (IV) that correspond to the compounds of Formula (II) with a suitable reagent (e.g. hydrogen peroxide or a peracid, such as m-chloroperbenzoic acid) as described in the examples provided herein.

The method for the synthesis of S-methyl-N,N-diethylthiolcarbamate sulfoxide (DETC-MeSO) that was reported in U.S. Pat. No. 5,153,219, actually gives a rearrangement isoform, S-methyl-O-(N,N-diethylcarbamoyl)sulfenate (DECOSMe) (FIG. 1). Some evidence that the material produced by this method is actually DECOSMe comes from the original mass spectral analysis provided in the patent covering thiocarbamate sulfoxides (Faiman et al., 1992: see U.S. Pat. No. 5,153,219). Six fragments are obtained from the preparation of DETC-MeSO, when it is subjected to chemical ionization ($NH_3$) mass spectroscopic analysis. The masses (M/Z) of the positively charged ions obtained and their relative abundance (in brackets) are: 164 (13), 148 (3), 100 (100), 72 (86) and 44 (82). The ion with a mass (M/Z) of 164 is identified as protonated ($M^{+1}$) DETC-MeSO, which could be obtained by gas-phase protonation of its sulfoxide moiety [$(C_2H_5)_2NC(O)S^+(OH)CH_3$]. The ions with masses (M/Z) of 100 and 72 are likely to be N,N-diethylisocyanate [$(C_2H_5)_2N^+CO$] and the radical cation of diethylamine [$(C_2H_5)_2N^+$], respectively, which can be formed from either DETC-MeSO or DECOSMe. However, the ions with masses (M/Z) of 148 and 44 are likely to be the radical cation of DECOSMe that has lost its methyl moiety [$(C_2H_5)_2NC(O)OS^+$] and the radical cation of carbon dioxide [$OCO^+$], respectively, which can only be formed from DECOSMe. Loss of the methyl substituent by DETC-MeSO would give a product of equivalent mass to the one obtained from DECOSMe, but it would more likely be protonated, in which case the M/Z would be 149 instead of 148. The relative abundance of the mass derived from DECOSMe with an M/Z of 44 (82/100) and the mass derived by protonation of DETC-MeSO ($M^{+1}$; 13/100), suggests that the mixture is composed of 72–87% DECOSMe and 13–18% DETC-MeSO. These values assume equal yields of these two unique ions from DECOSMe and DETC-MeSO, respectively. Since the yields of ions during mass spectroscopic analysis can be variable and have not been determined for these fragments, this is not a reliable method to determine the relative abundance of DECOSMe and DETC-MeSO in the mixture. Further, the ion with a mass of 44 could also be a carbon-sulfur cation ($C=S^+$). As such, the mass spectral data provided is not a reliable indicator of the rearrangement reaction illustrated in FIG. 1.

The invention also provides methods to increase the effectiveness of a therapeutic agent by linking the therapeutic agent to a compound of Formula (II). The compounds and pharmaceutical compositions of Formula (II) may be used to associate therapeutic agents with glutathione to increase the therapeutic efficiency of the therapeutic agent. The conjugation of glutathione to a compound of Formula (II) may be done in vitro (n=2). The compound of Formula (II) may also be conjugated to glutathione in vivo through administration of the compound of Formula (II) to a subject in need thereof, wherein the compound will undergo biological oxidation (n=0 or 1), rearrangement or spontaneous reaction (n=2) and be conjugated to endogenous glutathione within the subject.

The compounds of Formula (II) are also useful synthetic intermediates for association of therapeutic agents to glutathione; these glutathione conjugates have utility in improving delivery of these therapeutic agents in humans or animals for greater therapeutic benefit.

A method to distinguish a compound of Formula (II) from a compound of Formula (I) is also provided. In one embodiment, this method involves reacting a preparation with a suitable thiol and determining whether a reaction occurs between the thiol and a compound of Formula (I). Suitable thiols include thionitrobenzoates, such as 5-thio-2-nitrobenzoate, and other chromophoric thiols, such as p-nitrophenyl mercaptan, 2-pyridyl mercaptan or 4-pyridyl mercaptan. This method allows compounds of Formula (I) to be distinguished from compounds of Formula (II) because the suitable thiol will not react (n=0 or 1) or react much more slowly (n=2) with a compound of Formula (II). It is understood by those of skill in the art that the method includes the use of any compound that reacts differently with a compound of Formula (I) than with a compound of Formula (II) to produce a detectable result.

Such a method was used to determine that the original method described for preparation of DETC-MeSO (U.S. Pat. No. 5,153,219) in fact produces DECOSMe. Comparison of the $^1$H NMR spectra presented in U.S. Pat. No. 5,153,219 with those of authentic DETC-MeSO and DECOSMe as prepared herein, confirms that the original preparation was of DECOSMe and not DETC-MeSO. The reported reaction of compounds of Formula (II) wherein n is 1 with glutathione is not due to compounds of Formula (II), but due to the fact that these preparations actually contained compounds of Formula (I). Reaction of compounds of Formula (II) wherein n is 2 is much slower (1/50) than previously thought (U.S. Pat. No. 6,156,794) due to the presence of compounds of Formula (I) in these preparations.

It is likely that the preparations of DETC-MeSO used in U.S. Pat. Nos. 5,153,219 and 6,156,794 contained no DETC-MeSO, but were composed solely of DECOSMe. The following examines the various lines of evidence:

Mass spectroscopy: The presence of a mass (M/Z) of 164 has been interpreted as being derived from gas phase protonation of DETC-MeSO [$(C_2H_5)_2NC(=O)S^+(OH)CH_3$]. However, it could also be derived from the iminol form of DECOSMe [$(C_2H_5)_2N^+=C(OH)OSCH_3$]. This interpretation is consistent with the observation of a similar ion form in the mass spectrum of DETC-Me [$M^{+1}$ 148, $(C_2H_5)_2N^+=C(OH)SCH_3$]. If the mass of 164 can be derived from DECOSMe, then it does not provide evidence for the presence of DETC-MeSO.

HPLC: Since DETC-MeSO and DECOSMe are not resolved by the analytical methods employed in U.S. Pat. Nos. 5,153,219 and 6,156,794 (as demonstrated in EXAMPLE 7), they would only ascertain purity with respect to other compounds. These criteria would not distinguish between DETC-MeSO and DECOSMe.

Thionitrobenzoate: The chemical analysis employing reaction of DECOSMe with thionitrobenzoate (described herein, EXAMPLE 8) is the only evidence that the method of preparation described in U.S. Pat. Nos. 5,153,219 or 6,156,794 gave any DETC-MeSO (20%). However, this is essentially negative evidence and depends on the assumption that DECOSMe consumes thionitrobenzoate with 100% efficiency. It is just as likely that the reaction underestimates the content of DECOSMe for other reasons (e.g., competing hydrolysis of the carbamoyl sulfenate). If thionitrobenzoate does not react with DECOSMe in perfect 1:1 stoichiometry, then there is essentially no evidence that the DETC-MeSO preparations as described in U.S. Pat. Nos. 5,153,219 and 6,156,794 in fact contained any DETC-MeSO. The preparations used could have been composed solely of DECOSMe.

NMR: This is the strongest evidence that the preparations of DETC-MeSO described in U.S. Pat. Nos. 5,153,219 and 6,156,794 were composed exclusively of DECOSMe. As summarized in Table 1, the $^1$H NMR spectra of DETC-MeSO and DECOSMe are sufficiently different that NMR can distinguish these two compounds. In particular, the positions of the methylene protons on the carbons attached to nitrogen are well resolved spectrally (δ centered at 3.01 and 3.42 for DETC-MeSO compared to 3.47 and 3.61 for DECOSMe). The $^1$H NMR data presented in U.S. Pat. No. 5,153,219 have δ centered at 3.41 and 3.51; the entire spectra appears to be shifted by about 0.07 relative to standard position, which would give adjusted values of 3.48 and 3.58) more closely match the spectral data for DECOSMe. The primary strength of these data lies in the fact that they are quantitative. If 20% of the preparation described in U.S. Pat. No. 5,153,219 contained DETC-MeSO, then it would have been observed in the $^1$H NMR spectrum. The limit for detection of the other isomer by this method ($^1$H NMR) should be less than 10%. It is reasonable to conclude, based on the $^1$H NMR spectra that the preparation of DETC-MeSO described in U.S. Pat. No. 5,153,219 contained only DECOSMe (>95%). There is no compelling evidence presented that the preparation contained anything other than DECOSMe.

TABLE 1

Comparison of the $^1$H NMR(δ, CDCl$_3$) of DETC-Me, DETC-MeSO, DECOSMe, DETC-MeSO$_2$ and values reported in U.S. Pat. No. 5,153,219 for DETC-MeSO

| DETC-Me 400 MHz δ, CDCl$_3$ | DETC-MeSO 400 MHz δ$^1$, CDCl$_3$ | DECOSMe 400 MHz δ$^2$, CDCl$_3$ | 5,153,219 500 MHz δ, CDCl$_3$ | DETC-MeSO$_2$ 400 MHz δ, CDCl$_3$ |
|---|---|---|---|---|
| 1.18 (s, 6H) | 1.25 [0.08] (t, 3H) | 1.23 [0.06] (t, 3H) | 1.17 (t, 3H) | 1.24 (t, 3H) |
|  | 1.36 [0.13] (t, 3H) | 1.29 [0.06] (t, 3H) | 1.23 (t, 3H) | 1.31 (t, 3H) |
| 2.31 (t, 3H) | 2.73 [0.02] (s, 3H) | 2.78 [0.07] (s, 3H) | 2.71 (s, 3H) | 3.13 (s, 3H) |
|  | 3.01 [−0.31] (q, 2H) | 3.47 [0.06] (dq, 2H) | 3.41 (m, 2H) | 3.40 (q, 2H) |
| 3.39 (broad, 4H) | 3.42 [−0.09] (q, 2H) | 3.61 [0.10] (dq, 2H) | 3.51 (m, 2H) | 3.75 (q, 2H) |

$^1$The value in brackets is the difference obtained when the δ value presented for DETC-MeSO in U.S. Pat. No. 5,153,219 is subtracted from the corresponding δ value for DETC-MeSO reported herein.
$^2$The value in brackets is the difference obtained when the δ value presented for DETC-MeSO in U.S. Pat. No. 5,153,219 is subtracted from the corresponding δ value for DECOSMe reported herein.
NOTE:
The average difference between the δ values for DECOSMe and for the corresponding values reported in U.S. Pat. No. 5,153,219 is 0.07 ± 0.02 (range = 0.06 to 0.10), compared to the average difference between the δ values for DETC-MeSO and for the corresponding values reported in U.S. Pat. No. 5,153,219 is −0.03 ± 0.17 (range = −0.31 to 0.13). If only the differences for the methyl δ values are considered (those that would be perturbed the least by rearrangement of a thioester to a sulfenate), then the average difference between the δ values for DETC-MeSO and the corresponding values reported in U.S. Pat. No. 5,153,219 is 0.08 ± 0.05 (range = 0.02 to 0.13). Clearly, the $^1$H NMR values reported in U.S. Pat. No. 5,153,219 more closely match those for DECOSMe than they do for DETC-MeSO. This difference is most evident in the values for the methylene hydrogens attached to nitrogen, where for DETC-MeSO the values are centered at δ 3.01, compared to 3.47 for DECOSMe and 3.41 for U.S. Pat. No. 5,153,219.

III. Compounds of Formula (III)

The invention provides compounds of Formula (III). These compounds may be used to treat glutamate-related diseases, such as those described herein. Such compounds are able to be used for directed delivery of a therapeutic agent to a desired location within the body of an organism, particularly across the blood-brain barrier.

The invention also provides pharmaceutical compositions containing compounds of Formula (III). These pharmaceutical compositions may be formulated to suit any desired purpose. Examples of such formulations are disclosed herein.

The invention also provides methods for treating a glutamate-related disease by administration of an effective amount of a compound of Formula (III). The methods may involve administration of a compound of Formula (III) as described herein, alone, in a pharmaceutical composition, or in combination with other therapeutic agents and pharmaceutical compositions.

The invention also provides methods to deter ethanol consumption by administration of an effective amount of a compound of Formula (III) as described herein (see U.S. Pat. No. 5,153,219 and U.S. Pat. No. 6,156,794).

Also provided is a method for preparing a compound of Formula (III). These methods generally involve reaction of glutathione with a compound of Formula (II) to form a conjugate. Alternatively, the methods can involve reaction of glutathione with a compound of Formula (II) that has undergone rearrangement to form the corresponding compound of Formula (I). Such methods are described herein (see Examples 1–11).

The invention also provides methods to increase the effectiveness of a therapeutic agent by forming a compound of Formula (III) that includes the therapeutic agent.

The invention will be further described by reference to the following detailed examples. It is understood that the examples are not meant to limit the scope of the invention in any way.

EXAMPLE 1

S-Methyl-N,N-Diethylthiolcarbamate (DETC-Me)

DETC-Me was synthesized employing a modification of the method of P. Klason, *J. Prak. Chemie,* 36, 67 (1887). Carbonyl sulfide, produced by dripping saturated KSCN into 48% sulfuric acid, was bubbled into a mixture of 57.2 ml of triethylamine and 14.1 ml of diethylamine in 300 mL of $CH_2Cl_2$ in a 500 ml round bottom flask. The solution was stirred as the gas bubbled through the amine solution at $-78°$ C., with the reaction proceeding for 1 hour. The reaction was terminated by adding 17.0 ml of methyl iodide over a period of 30 minutes and the mixture was maintained at $-78°$ C. for 2.5 hours to form the final methylated product. After 45 minutes, the reaction mixture was filtered and the methylene chloride and other volatile materials were evaporated. The remaining oil phase was dissolved in diethyl ether, filtered, and the ether and other volatile materials were evaporated. The resulting organic phase was dried over sodium sulfate, and evaporated in vacuo to give 23.6 g of an oil. DETC-Me was purified by vacuum distillation. Distillation is obtained between 73–80° C. at a pressure of 4.5 mm of mercury. The structure was verified by TLC, NMR [$^1$H NMR (400 MHz, $CDCl_3$) δ1.1755 (s,6H), 2.3061–2.3182 (t,3H), 3.3916 (broad,4H)], and mass spectroscopy [ESMS (relative intensity) 148 ($M^{+1}$, $(C_2H_5)_2N^+$=C(OH)$SCH_3$, 12) and 100 (100)].

EXAMPLE 2

S-Methyl-N,N-Diethylthiolcarbamate Sulfoxide (DETC-MeSO)

To 10 g of DETC-Me in 100 ml of glacial acetic acid were added 5.2 ml of 30% hydrogen peroxide. This reaction mixture was incubated at 4° C. for 2 days, at which time analysis by thin layer chromatography indicated about 50% of the DETC-Me had been converted to DETC-MeSO. Glacial acetic acid was eliminated by rotary evaporation. The sample was redissolved in approximately 100 ml of acetone and subjected to rotary evaporation several times to eliminate residual water in the sample. Separation of DETC-MeSO from residual DETC-Me was achieved by distillation in vacuo. The sample was placed in a flask at 55° C. under vacuum and the volatile DETC-Me was collected as a solid in a liquid nitrogen trap. The structure was verified by TLC, NMR ($^1$H NMR (400 MHz, $CDCl_3$) δ1.23561–1.27099 (t,3H), 1.33796–1.37435 (t,3H), 2.73306 (s,3H), 2.98944–3.02588 (q,2H), 3.39336–3.44365 (q,2H)), and mass spectroscopy [ESMS (relative intensity) 164 ($M^{+1}$, 11) and 100 (N,N-diethylisocyanate$^+$, 100)].

In the mass spectrum of DETC-MeSO (ESMS) there was no detectable peak with a mass (M/Z) of 44. Since the mass of 44 could be diagnostic for rearrangement of DETC-MeSO to S-methyl-O-(N,N-diethylcarbamoyl)sulfenate (DECOSMe), the protonated parent ion (M/Z=164) was selected and subjected to further fragmentation analysis by MS-MS. When the protonated sulfoxide [164, $(C_2H_5)_2NC(=O)S^+(OH)CH_3$] was selectively subjected to impact fragmentation (impact-induced rearrangement, with concomitant fragmentation) in a second round of mass spectral analysis, masses of 100 [N,N-diethylisocyanate$^+$, $(C_2H_5)_2N^+$=C=O], 72 [the radical cation of diethylamine, $(C_2H_5)_2N^+$], and 44 [the radical cation of carbon dioxide, O=C=$O^+$, or a S=$C^+$ fragment] were obtained. Further selection and fragmentation of the peak with a mass (M/Z) of 44, in a third round of mass spectral analysis by MS-MS-MS, gave a mass of 28 (O=$C^+$). This allows identification of the mass with an M/Z of 44 as the radical cation of carbon dioxide, rather than a fragment of similar mass composed of one carbon atom and one sulfur atom (S=$C^+$). DETC-MeSO can rearrange into DECOSMe (induced, in this instance, by collision) and fragmentation of the latter gives a mass (M/Z) of 44. Clearly, migration of the carbamoyl moiety from sulfur (DETC-MeSO) to oxygen (DECOSMe) produces the structure that can fragment to give carbon dioxide (M/Z=44).

The $^1$H NMR spectrum of authentic DETC-MeSO as synthesized here (EXAMPLE 2) is distinct from the spectrum of the sample previously reported to be DETC-MeSO in U.S. Pat. No. 5,153,219. Comparison of the $^1$H NMR spectra for DETC-Me (EXAMPLE 1), DETC-MeSO (EXAMPLE 2), DECOSMe (EXAMPLE 4), and DETC-MeSO$_2$ (EXAMPLE 5) is provided in Table 1. Careful comparison of these $^1$H NMR spectra allow identification of the sample in U.S. Pat. No. 5,153,219 as DECOSMe, rather than DETC-MeSO as claimed.

EXAMPLE 3

Use of Acetic Anhydride to Facilitate Oxidation with Hydrogen Peroxide

Hydrogen peroxide oxidized DETC-Me to DETC-MeSO in glacial acetic acid. To test whether this might be due to formation of peracetic acid ($CH_3C(=O)OOH$), the effect of acetic anhydride on this oxidation was examined. Two samples were prepared for mass spectral analysis. In the first sample, 0.1 ml of DETC-Me, 1 ml of glacial acetic acid, and 0.052 ml of 30% hydrogen peroxide were mixed in a plastic container and incubated at 4° C. In a second sample, 0.1 ml of DETC-Me, 1 ml of glacial acetic acid, 0.052 ml of 30% hydrogen peroxide, and 0.052 ml of acetic anhydride were mixed in a plastic container and incubated at 4° C. In the sample that did not contain acetic anhydride, electrospray mass spectral analysis detected masses of 164 ($M^{+1}$, DETC-MeSO) and 148 ($M^{+1}$, DETC-Me) with relative intensities of 7.40% and 3.68%, respectively, compared to the mass of 100 (diethylisocyanate). In the sample that contained acetic anhydride, the corresponding intensities of masses 164 and 148 were 11.2% and 1.18%, respectively. The presence of acetic anhydride in 1:1 ratio with hydrogen peroxide increased the yield of DETC-MeSO from 69% ($H_2O_2$ alone)

to 90% (1:1 acetic anhydride:$H_2O_2$). Acetic anhydride improves the yield of thioester oxidation obtained in $H_2O_2$-acetic acid.

EXAMPLE 4

Rearrangement of DETC-MeSO to S-Methyl-O-(N,N-Diethylcarbamoyl)Sulfenate (DECOSMe)

Rearrangement of DETC-MeSO (0.5 g) to DECOSMe was obtained by subjecting DETC-MeSO (EXAMPLE 2) to medium pressure chromatography (C-18 Sepralite® 40 μm, mobile phase 1:1 acetonitrile-$H_2O$). Fractions containing DECOSMe were pooled and extracted with methylene chloride. The solvent was dried with sodium sulfate and removed under reduced pressure to yield 0.46 g of DECOSMe as a yellowish oil. In an alternate method, DECOSMe could be obtained by subjecting DETC-MeSO to flash silica chromatography. DETC-MeSO (0.5 g) was dissolved in a minimum amount of methylene chloride and subjected to low pressure chromatography (flash silica gel type C, 220–420 mesh, from Selecto Scientific, using isocratic gradient solvent: acetonitrile 5–10%, methylene chloride 90–95%). Fractions containing DECOSMe were pooled, dried with sodium sulfate and the solvent removed under reduced pressure to yield 0.40 g of DECOSMe as a yellowish oil. The structure was verified by TLC, NMR [$^1$H NMR (400 MHz, $CDCl_3$) δ1.23 (t,3H), 1.29 (t,3H), 2.78 (s,3H), 3.47 (q,2H), 3.61 (q,2H)], and mass spectroscopy [CIMS ($NH_3$) M/Z (relative intensity), 164 ($M^{+1}$,13), 148 (3), 100 (100), 72 (86), 44 (82)].

EXAMPLE 5

S-Methyl-N,N-Diethylthiolcarbamate Sulfone (DETC-$MeSO_2$)

To 2 g of DETC-Me in 200 ml of methylene chloride at 4° C. were added 4.7 g of m-chloroperbenzoic acid (Aldrich Chemical Company) with stirring. After incubating for 1 hr at 4° C., conversion of DETC-Me to DETC-$MeSO_2$ was confirmed by thin layer chromatographic analysis. Incubation of the reaction mixture overnight at −20° C. resulted in the formation of a white precipitate that was eliminated by filtration. The reaction mixture was extracted several times with aqueous saturated sodium bicarbonate, dried over anhydrous magnesium sulfate and rotary evaporated in vacuo to give 2.15 g of a light green oil (86% yield). This material may be used without further purification. The structure was verified by TLC and NMR [$^1$H NMR (400 MHz, $CDCl_3$) δ1.22838–1.24584 (t,3H), 1.30160–1.31876 (t,3H), 3.13423 (s,3H), 3.36569–3.42723 (q,2H), 3.72321–3.77416 (q,2H)].

EXAMPLE 6

S-(N,N-Diethylcarbamoyl)Glutathione (Carbamathione)

To 32.54 g of glutathione (106 mmole) were added 200 ml of water and 3.91 g of lithium carbonate (53 mmole). After completion of effervescence due to release of carbon dioxide, carbamoylation of glutathione was initiated by addition of 30 ml of DETC-$MeSO_2$ (32.2 g, 180 mmole, 1.7 equivalents of carbamoyl thioester sulfone per mercaptan) at room temperature. Six minutes after the addition of DETC-$MeSO_2$, the free mercaptan content of the reaction mixture had fallen to 68% of its initial value (by assay with 5,5'-dithiobis(2-nitrobenzoic acid)). An additional 3.91 g of lithium carbonate (53 mmole) were added to facilitate completion of the reaction by neutralization of the methyl sulfinic acid produced in the reaction of DETC-$MeSO_2$ with glutathione. After allowing the sample to incubate at room temperature for an additional 30 minutes, the free mercaptan content of the reaction mixture had fallen to less than 0.2% of its initial value and the solution was neutral (approximately pH 7). Hydrochloric acid (212 ml of 1 N, 212 mmole) was added to the reaction mixture to convert carbamathione to its zwitterionic form (similar to the starting material, glutathione), protonate the methyl sulfinate, convert lithium to its chloride salt and lower the pH of the reaction mixture to about 2. The reaction mixture was mixed with 3 l of 95% ethanol and incubated at 4° C. for several days to allow carbamathione to crystallize from the mixture. Other products present in the reaction mixture (lithium chloride, methyl sulfinic acid and residual DETC-$MeSO_2$) were soluble in the water-ethanol mixture. Carbamathione was collected by filtration and washed with cold (4° C.) ethanol. After drying in a dessicator under vacuum, 31 g (76 mmole) of crystalline carbamathione (72% yield) was obtained. The sample was analytically pure as judged by NMR: [$^1$H NMR (400 MHz) δ0.86375–1.14953 (m,6H), 2.02372–2.07725 (m,2H), 2.39394–2.45211 (m,2H), 3.07967–3.13693 (m,1H), 3.28858–3.37060 (m,5H), 3.67051–3.70170 (t,1H). 3.84321 (s,2H), 4.51792–4.55018 (t,1H)], mass spectroscopy: [ESMS 407], and elemental analysis (weight percent): [expected: (44.32) C, (6.45) H, (13.78) N, (7.89) S. found: (44.01) C, (6.43) H, (13.26) N, (7.95) S].

EXAMPLE 7

Chromatographic Analysis of DETC-MeSO and DECOSMe

When DETC-MeSO (EXAMPLE 2) or DECOSMe (EXAMPLE 4) are subjected reverse phase chromatography by HPLC they both give a single peak with a coincident elution time. On the same column (2 cm×22 cm, C-18 Sepralite® 40 μm, mobile phase 25% acetonitrile/water, 1.0 ml/min, compounds detected by monitoring the eluant at 215 nm) DETC-MeSO and DECOSMe have retention times of 3.67 minutes, glutathione and carbamathione have retention times of 1.8 and 2.2 minutes, respectively. If DECOSMe (EXAMPLE 4) were a mixture of DECOSMe and DETC-MeSO (see EXAMPLE 8), two peaks would be obtained in any chromatographic system, if these two isomers were resolved. If DECOSMe and DETC-MeSO were mixed in equal amounts (1:1) prior to analyzing this new mixture (with equal amounts of DECOSMe and DETC-MeSO), then a single chromatographic peak (of equivalent size and retention time to that obtained when either DECOSMe or DETC-MeSO were analyzed alone) was obtained.

EXAMPLE 8

Quantitative Detection of DECOSMe and Other Thiol-Reactive Substances

A stock solution of 5-thio-2-nitrobenzoate (hereafter referred to as thionitrobenzoate) was prepared by reduction of 5,5'-dithiobis(2-nitrobenzoic acid) (hereafter referred to as DTNB, Aldrich Chemical Company). This stock solution was prepared by mixing 0.1 ml of 0.1 M DTNB dissolved in ethanol (396 mg of DTNB in 10 ml of ethanol), 0.1 ml of 1 M aqueous potassium phosphate buffer (prepared by mixing equal volumes of 1 M monobasic potassium phosphate with 1 M dibasic potassium phosphate), and 0.025 ml of 1 M sodium borohydride dissolved in 1 M NaOH on ice. After incubating this mixture for 10 minutes at ice temperature, 0.1 mL of 1 M monobasic potassium phosphate was added and the resultant solution was diluted to a final volume of 2 ml by addition of 1.675 ml of water. The stock solution had a final concentration of 10 mM thionitrobenzoate.

An alternate method for preparation of a stock solution of thionitrobenzoate involves the use of 2-mercaptoethanol as reductant, in place of sodium borohydride. In this method a 10 mM solution of DTNB was prepared by mixing 39.6 mg of DTNB with 17 mg of sodium bicarbonate and 4 ml of ice-cold water. After allowing the effervescence to subside, this solution was mixed with 0.01 ml of 0.5 M trisodium ethylenediaminetetracetate and 0.1 ml of 1 M potassium phosphate buffer, then diluted to a final volume of 10 ml with water. A separate stock of 10 mM 2-mercaptoethanol was prepared by dilution of neat 2-mercaptoethanol (14.3 M) with water (serial dilution of 0.01 ml of neat 2-mercaptoethanol to 1 ml to give 0.143 M and then dilution of 0.07 ml of this solution to a final volume of 1 ml to give 10 mM). The stock of 8.7 mM thionitrobenzoate was prepared by mixing 2 ml of 1 M potassium phosphate buffer with 0.2 ml of 10 mM 2-mercaptoethanol and 0.1 ml of 10 mM aqueous DTNB.

For purposes of determining DECOSMe or other thiol-reactive substances, the two thionitrobenzoate stocks (prepared by reduction of DTNB with borohydride or mercaptoethanol) gave comparable results. If 0.01 ml of the 10 mM stock of thionitrobenzoate, obtained by sodium borohydride reduction of DTNB, was diluted with 0.89 ml of water and 0.1 ml of 1 M phosphate buffer, it gave an absorbance at 412 nm of 1.36 in a 1 cm pathlength cuvette. If 0.01 ml of the 8.7 mM stock of thionitrobenzoate obtained by 2-mercaptoethanol reduction of DTNB was diluted with 0.89 ml of water and 0.1 ml of 1 M phosphate buffer, it gave an absorbance at 412 nm of 1.18 in a 1 cm pathlength cuvette. Addition of 0.01 ml of a 0.1 M aqueous solution of DECOSMe (EXAMPLE 4) to either of these solutions resulted in the first-order decay of absorbance at 412 nm with a half time of 2.9 minutes at a temperature of 25° C. (4 $M^{-1}$ $s^{-1}$). Addition of 0.01 ml of a 5 mM aqueous solution of DECOSMe to either of these solutions in an anaerobic cuvette (argon atmosphere) maintained at 25° C. resulted in a loss in absorbance of 0.54 at 412 nm within 6 hours. Further incubation of the solution for up to a total of 24 hours did not result in a further decrease in absorbance at 412 nm. By contrast, if 0.01 ml of a 5 mM aqueous solution of DETC-MeSO (EXAMPLE 2), which had been freshly synthesized and not subjected to chromatographic purification, was added to either of these assay mixtures of thionitrobenzoate, there were no changes in absorbance at 412 nm for up to 24 hours under anaerobic conditions, other than the immediate change observed on mixing due to dilution (0.01 absorbance unit). This indicated that the rate of reaction of DETC-MeSO, prior to rearrangement to DECOSMe, with thionitrobenzoate was less than 0.01 $M^{-1}$ $s^{-1}$.

DETC-Me (EXAMPLE 1), DETC-MeSO (EXAMPLE 2) and carbamathione (EXAMPLE 6) did not react with thionitrobenzoate in aqueous solution at pH 7 and 25° C. (<0.05 $M^{-1}$ $s^{-1}$). DECOSMe (EXAMPLE 4) reacted with thionitrobenzoate under these conditions at a rate of 4 $M^{-1}$ $s^{-1}$. DETC-MeSO$_2$ (EXAMPLE 5) reacted with thionitrobenzoate under these conditions at a rate of 0.4 $M^{-1}$ $s^{-1}$. S-Methyl-O-(N,N-diethylcarbamoyl)sulfinate (DECO$_2$SMe, prepared by rearrangement of DETC-MeSO$_2$ under the conditions described in EXAMPLE 4) reacted with thionitrobenzoate under these conditions at a rate of 14 $M^{-1}$ $s^{-1}$.

EXAMPLE 9

A General Method for Preparation of Compounds of Formula $(R^1)(R^2)NC(=O)S(\rightarrow O)_n R^3$ If n=1, approximately equimolar amounts of a thioester $[(R^1)(R^2)NC(=O)SR^3]$ and $H_2O_2$ may be combined in glacial acetic acid so that the concentration of each is about 0.5 M. One equivalent of acetic anhydride can be added to facilitate the oxidation. If n=2, then approximately two equivalents of $H_2O_2$ (0.5 M) and acetic anhydride (0.5 M) are combined with the thioester (0.25 M). After 24 hours at 4° C., glacial acetic acid may be removed by evaporation. Any residual water in the sample can be eliminated by suspending the sample in acetone and removing the acetone by evaporation.

EXAMPLE 10

A General Method for Preparation of Compounds of Formula $(R^1)(R^2)NC(=O)OS(\rightarrow O)_n R^3$ If n=0 or 1, then a compound of the formula $(R^1)(R^2)NC(=O)S(\rightarrow O)_m R^3$, where m=(n+1) is brought into contact with powdered silica, such as flash silica gel type C, 220–420 mesh, from Selecto Scientific. This contact can be conducted by mixing the compound with the powdered silica at a ratio of about 1:100 $[(R^1)(R^2)NC(=O)S(\rightarrow O)_m R^3$: powdered silica]. After 60 minutes at an appropriate temperature, such as room temperature, the rearrangement mixture can be eluted from the silica with a suitable solvent, such as $CH_2Cl_2$; the silica separated by filtration, and the solvent removed by evaporation. This contact can also be conducted by carrying out chromatography of the compound of formula $(R^1)(R^2)NC(=O)S(\rightarrow O)_m R^3$ on a flash silica or C-18 coated silica as described in EXAMPLE 7. If $R^1$ and $R^2$ are individually methyl or ethyl, then the ratio of compound of formula $(R^1)(R^2)NC(=O)OS(\rightarrow O)_n R^3$ to compound of formula $(R^1)(R^2)NC(=O)S(\rightarrow O)_m R^3$ in the mixture will be greater than 1. If $R^1$ and $R^2$ are individually composed of three or more carbons, then the ratio of compound of formula $(R^1)(R^2)NC(=O)OS(\rightarrow O)_n R^3$ to compound of formula $(R^1)(R^2)NC(=O)S(\rightarrow O)_m R^3$ in the mixture will be less than 1. If n=0, then the precise content of compound of formula $(R^1)(R^2)NC(=O)OS(\rightarrow O)_n R^3$ in the mixture can be determined as described in EXAMPLE 8. If n=1, then the total content of compound of formula $(R^1)(R^2)NC(=O)OS(\rightarrow O)_n R^3$ and compound of formula $(R^1)(R^2)NC(=O)S(\rightarrow O)_{(n+1)} R^3$ can be determined as described in EXAMPLE 8. If n=2, then the compound of formula $(R^1)(R^2)NC(=O)OS(\rightarrow O)_2 R^3$ may be prepared by oxidation of a compound of formula $(R^1)(R^2)NC(=O)OS(\rightarrow O)R^3$ as described in EXAMPLE 9.

EXAMPLE 11

A General Method for Preparation of Glutathione Conjugates

A slight excess (1.05–2 equivalents) of a molecule of formula $(R^1)(R^2)NC(=O)S(\rightarrow O)_n R^3$, wherein n=2, or a compound of formula $(R^1)(R^1)NC(=O)OS(\rightarrow O)_m R^3$, wherein m=1 or 2, (and wherein $R^1$, $R^2$, and $R^3$ have the definitions given herein, or individually $R^1$ or $R^2$ contain a therapeutic agent) and glutathione are mixed in water at a final concentration of about 0.05 M. Two equivalents of a base (such as lithium carbonate or lithium bicarbonate, i.e., 0.05 M $Li_2CO_3$ or 0.1 M $LiHCO_3$) are added to neutralize the glutathione and the acid produced by the reaction of glutathione and the carbamoylating agent. After 30 minutes at 4° C., about two equivalents of a strong acid, such as HCl (e.g., 0.1 M HCl) may be added to acidify the reaction mixture. The glutathione can then be collected by the addition of a water miscible solvent, such as ethanol, to induce crystallization of the glutathione conjugate on standing at an appropriate temperature, such as 4° C. Crystals of the conjugate can be collected by filtration or centrifugation and washed with the crystalization solvent before drying in vacuo. A molecule of formula $(R^1)(R^2)NC(=O)OS(\rightarrow O)_m R^3$, wherein m=0, will give oxidized glutathione as a side product when used as the carbamoylating agent. The presence of oxidized glutathione in the final product necessitates the use of chromatographic purification techniques or more complex chemical schemes to regenerate reduced glutathione from the oxidized glutathione.

All publications, patents, and patent documents are incorporated by reference herein, as though individually incorporated by reference. The invention has been described with reference to various specific preferred embodiments and techniques. However, it should be understood that many variations and modifications may be made while remaining within the spirit and scope of the invention.

What is claimed is:

1. A compound of Formula (III):

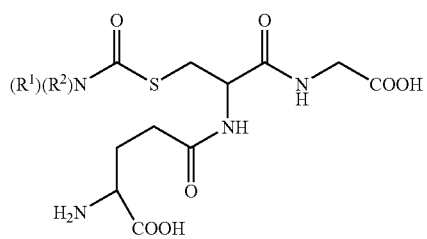

(III)

wherein:

a) $R^1$ and $R^2$ are individually D or -L-D;

each D is independently a therapeutic agent;

each L is independently a linking group;

or a pharmaceutically acceptable salt thereof.

2. A compound of Formula (III):

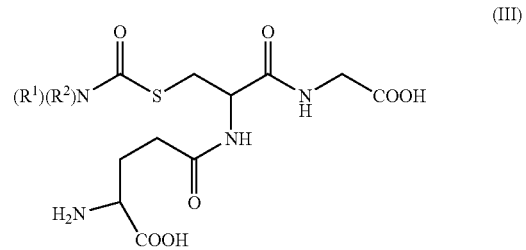

(III)

wherein:

$R^1 R^2 N$ taken together are D, wherein D is a therapeutic agent, or a pharmaceutically acceptable salt thereof.

3. A compound of claim 1, wherein $R^1$ and $R^1$ are each independently D.

4. A compound of claim 1, wherein $R^1$ and $R^1$ are each independently -L-D.

5. A pharmaceutical composition comprising a therapeutically effective amount of a compound of Formula (III) as described in claim 1 or 2 or a pharmaceutically acceptable salt thereof and a pharmaceutically acceptable carrier.

6. The pharmaceutical composition of claim 5, which is formulated as an ingestible capsule that passes the stomach before releasing its contents in the intestine.

7. A method for treatment of a glutamate-related disease in a mammal treatable by administration of a compound of Formula (III) comprising administering to the mammal a therapeutically effective amount of a compound of Formula (III) as described in claim 1 or 2 or a pharmaceutically acceptable salt thereof, wherein the glutamate-related disease is alcohol addiction, cocaine addiction, opioid addiction, acquired immunodeficiency syndrome neuropathy, Creutzfeldt-Jakob disease, noise-induced hearing loss, hepatic encephaolopathy, ammonia toxicity, cyanide-induced apoptosis, diabetic neuropathy, epilepsy, schizophrenia, nicotine addiction, anxiety, cerebral ischemia, cardiovascular ischemia, amphetamine addiction, nonketonic hyperglycinemia, bipolar disorder or Alzheimer's disease.

8. The method of claim 7, wherein the glutamate-related disease is noise-induced hearing loss.

9. A method for treatment of a disease in a mammal treatable by administration of D comprising administering a compound of Formula (III) as described in claim 1, or 2, or a pharmaceutically acceptable salt thereof.

10. The method of claim 9, wherein the mammal is a human.

11. A method to provocatively test for schizophrenia in a human comprising administering S-(N,N-diethylcarbamoyl) glutathione to the human and correlating the induction of a hallucination in the human with schizophrenia.

12. The method of claim 11, wherein the hallucinations is an auditory hallucination.

13. A method to increase the effectiveness of a therapeutic agent comprising linking the therapeutic agent to a compound of Formula (III) as described in claim 1 or 2.

14. A method to prepare a compound of Formula (III) as described in claim 1 or 2 comprising reacting a corresponding compound of Formula (II)

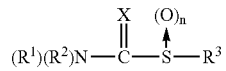

wherein n is 2 and X is O with glutathione.

15. The method of claim 14 further comprising adding a water miscible solvent to induce crystalization of the compound of Formula (III) to form a crystallized conjugate.

16. The method of claim 15, wherein the water miscible solvent is ethanol.

17. A compound of Formula (III) as described in claim 1 or 2 prepared by reacting a corresponding compound of Formula (II)

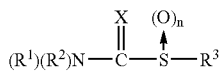

wherein n is 2 and X is O with glutathione.

* * * * *